US012622819B2

(12) United States Patent
Oshima

(10) Patent No.: US 12,622,819 B2
(45) Date of Patent: May 12, 2026

(54) DISPOSABLE DIAPER

(71) Applicant: DAIO PAPER CORPORATION,
Shikokuchuo (JP)

(72) Inventor: Aya Oshima, Sakura (JP)

(73) Assignee: DAIO PAPER CORPORATION,
Shikokuchuo (JP)

( * ) Notice: Subject to any disclaimer, the term of this
patent is extended or adjusted under 35
U.S.C. 154(b) by 322 days.

(21) Appl. No.: 18/560,529

(22) PCT Filed: Mar. 1, 2022

(86) PCT No.: PCT/JP2022/008523
§ 371 (c)(1),
(2) Date: Nov. 13, 2023

(87) PCT Pub. No.: WO2023/037584
PCT Pub. Date: Mar. 16, 2023

(65) Prior Publication Data
US 2024/0252367 A1 Aug. 1, 2024

(30) Foreign Application Priority Data
Sep. 13, 2021 (JP) ................................. 2021-148996

(51) Int. Cl.
*A61F 13/493* (2006.01)
*A61F 13/56* (2006.01)
*A61F 13/84* (2006.01)
(52) U.S. Cl.
CPC ........ *A61F 13/493* (2013.01); *A61F 13/5638*
(2013.01); *A61F 13/84* (2013.01); *A61F*
*2013/8497* (2013.01)
(58) Field of Classification Search
CPC ............ A61F 13/49014; A61F 13/5622; A61F
13/5638; A61F 13/56
See application file for complete search history.

(56) References Cited

U.S. PATENT DOCUMENTS

2004/0022998 A1* 2/2004 Miyamoto .......... A61F 13/5638
428/99
2007/0129700 A1* 6/2007 Yoshida .............. A61F 13/5644
604/391
(Continued)

FOREIGN PATENT DOCUMENTS

CA 2787540 A1 * 7/2011 .......... A61F 13/496
CN 104768512 A 7/2015
(Continued)

OTHER PUBLICATIONS

Office Action issued on Dec. 19, 2024, in corresponding Taiwanse
Application No. 111108393, 12 pages.
(Continued)

*Primary Examiner* — Adam Marcetich
*Assistant Examiner* — Ted Yang
(74) *Attorney, Agent, or Firm* — Maier & Maier, PLLC

(57) ABSTRACT

A disposable diaper includes a diaper body having a top
sheet, a back sheet, and an absorber disposed therebetween,
the disposable diaper extending from a backside portion to
an abdominal side portion; a side flap provided in each of
side portions of the backside portion, the side flap extending
outward beyond the absorber in a width direction; and a
fastening tape that is provided in the side flap to be fastened
to the abdominal side portion when the diaper body is used.
The fastening tape includes a fixed portion fixed to the side
flap, and a protruding piece extending outward from the
fixed portion in the width direction. The fixed portion
includes a notch in a lower region that is closer to a leg side
of a wearer than the protruding piece. The notch is recessed
from an outer edge in the width direction toward an inner
side.

3 Claims, 8 Drawing Sheets

(56) References Cited

U.S. PATENT DOCUMENTS

| | | | | |
|---|---|---|---|---|
| 2010/0280484 A1* | 11/2010 | Kline | A61F 13/5638 | 604/386 |
| 2012/0143166 A1* | 6/2012 | Kimura | A61F 13/15756 | 604/391 |
| 2012/0245548 A1* | 9/2012 | Matsushima | A61F 13/5638 | 604/389 |
| 2014/0236116 A1* | 8/2014 | Landgrebe | A61F 13/5638 | 156/60 |
| 2021/0145663 A1* | 5/2021 | Hayden | A61F 13/64 | |
| 2021/0236353 A1* | 8/2021 | Nagano | A61F 13/622 | |

FOREIGN PATENT DOCUMENTS

| | | | |
|---|---|---|---|
| CN | 112105324 A | 12/2020 | |
| EP | 3804682 A1 | 4/2021 | |
| FR | 2714288 A1 * | 6/1995 | ....... A61F 13/49015 |
| JP | 2010136788 A | 6/2010 | |
| JP | 2012120663 A | 6/2012 | |
| JP | 2013172814 A * | 9/2013 | |
| JP | 2014111042 A | 6/2014 | |
| JP | 2017063942 A | 4/2017 | |
| JP | 2019205538 A | 12/2019 | |
| JP | 2021074077 A | 5/2021 | |
| KR | 1020210014099 A | 2/2021 | |
| TW | 201800071 A | 1/2018 | |
| WO | 2014073511 A1 | 5/2014 | |
| WO | WO-2019230331 A1 * | 12/2019 | ............ A61F 13/56 |

OTHER PUBLICATIONS

International Search Report issued on Apr. 19, 2022, in corresponding International Application No. PCT/JP2022/008523, 5 pages.

* cited by examiner

DISPOSABLE DIAPER

CROSS-REFERENCE TO RELATED APPLICATION

The present application is based upon and claims the benefit of priority of Japanese Patent Application No. 2021-148996, filed with the Japan Patent Office on Sep. 13, 2021, the entire disclosure of which is completely incorporated herein by reference.

TECHNICAL FIELD

The present disclosure relates to a disposable diaper.

BACKGROUND

A disposable diaper with fastening tapes that fasten a backside portion and an abdominal side portion of a diaper body at the time of wearing the diaper is known (see, for example, Patent Literature 1: JP 2010-136788 A, Patent Literature 2: JP 2012-120663 A, and Patent Literature 3: JP 2021-074077 A). Here, in a conventional disposable diaper, a diaper body includes a side flap on each side of a backside portion, and each fastening tape includes a fixed portion fixed to the side flap and a protruding piece extending from the fixed portion to an outside of the diaper body in a width direction. In addition, Patent Literatures 1 and 2 disclose a configuration in which a cutout or notch is formed in the fixed portion, wherein the notch is recessed from an inside edge of the diaper body in the width direction toward an outside in the width direction. Furthermore, Patent Literature 3 discloses a configuration in which the fixed portion extends below the protruding piece (toward a leg side of a wearer).

SUMMARY

Meanwhile, the fixed portion of the fastening tape disclosed in Patent Literatures 1 and 2 does not extend below the protruding piece (toward the leg side of the wearer). Therefore, when the backside portion and the abdominal side portion are tied together, a force that acts on a lower portion of the side flap is weakened to reduce the fit of the diaper body around the legs.

Furthermore, in the fastening tape disclosed in Patent Literature 3, the fixed portion extends below the protruding piece (toward the leg side of the wearer). This extension of the fixed portion increases the rigidity of a part of the side flap that is lower than the protruding piece. Therefore, when the backside portion and the abdominal side portion are fastened together, and the lower portion of the side flap is not deformed properly, which reduces the fit of the diaper body around the legs.

In view of the above, it is an object of the present disclosure to provide a disposable diaper capable of improving the fit of a diaper body around the legs.

To achieve the object described above, a disposable diaper of the present disclosure includes a diaper body that includes a front surface sheet, a back surface sheet, and an absorber disposed between the front surface sheet and the back surface sheet, the diaper body extending from a backside portion of the diaper body to an abdominal side portion of the diaper body: a side flap that is provided in each of side portions of the backside portion, the side flap extending outward beyond the absorber in a width direction of the diaper body: and a fastening tape that is provided in the side flap to be fastened to the abdominal side portion when the diaper body is used. The fastening tape includes a fixed portion that is fixed to the side flap; and a protruding piece that extends outward from the fixed portion in the width direction. The fixed portion includes a notch in a lower region of the fixed portion that is closer to a leg side of a wearer than the protruding piece, the notch being recessed from an outer edge in the width direction toward an inner side in the width direction.

DETAILED DESCRIPTION

Figure 1:
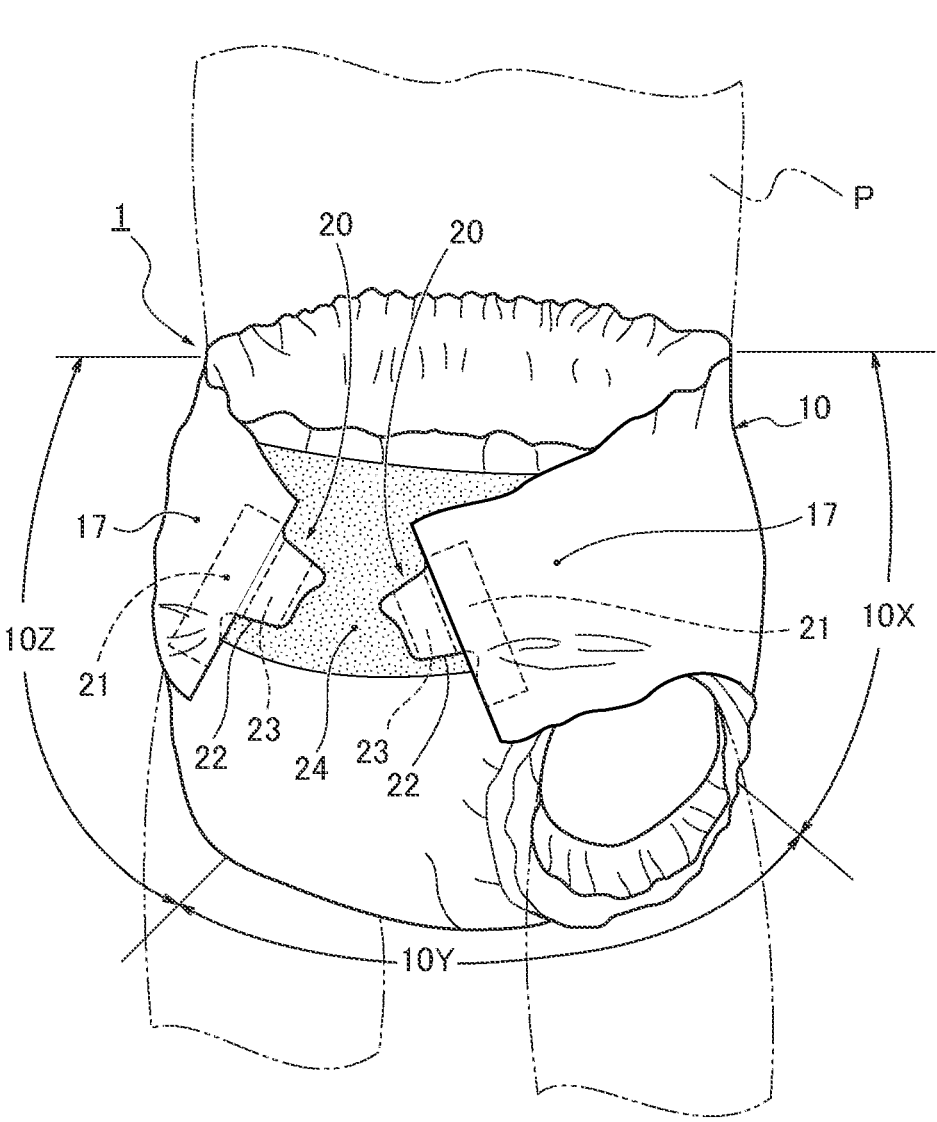
FIG. 1 is an external perspective view illustrating the state of use of a disposable diaper in Example 1.

A disposable diaper according to the present disclosure is described with reference to Examples 1 and 2 illustrated in the drawings.

Example 1

Figure 2:
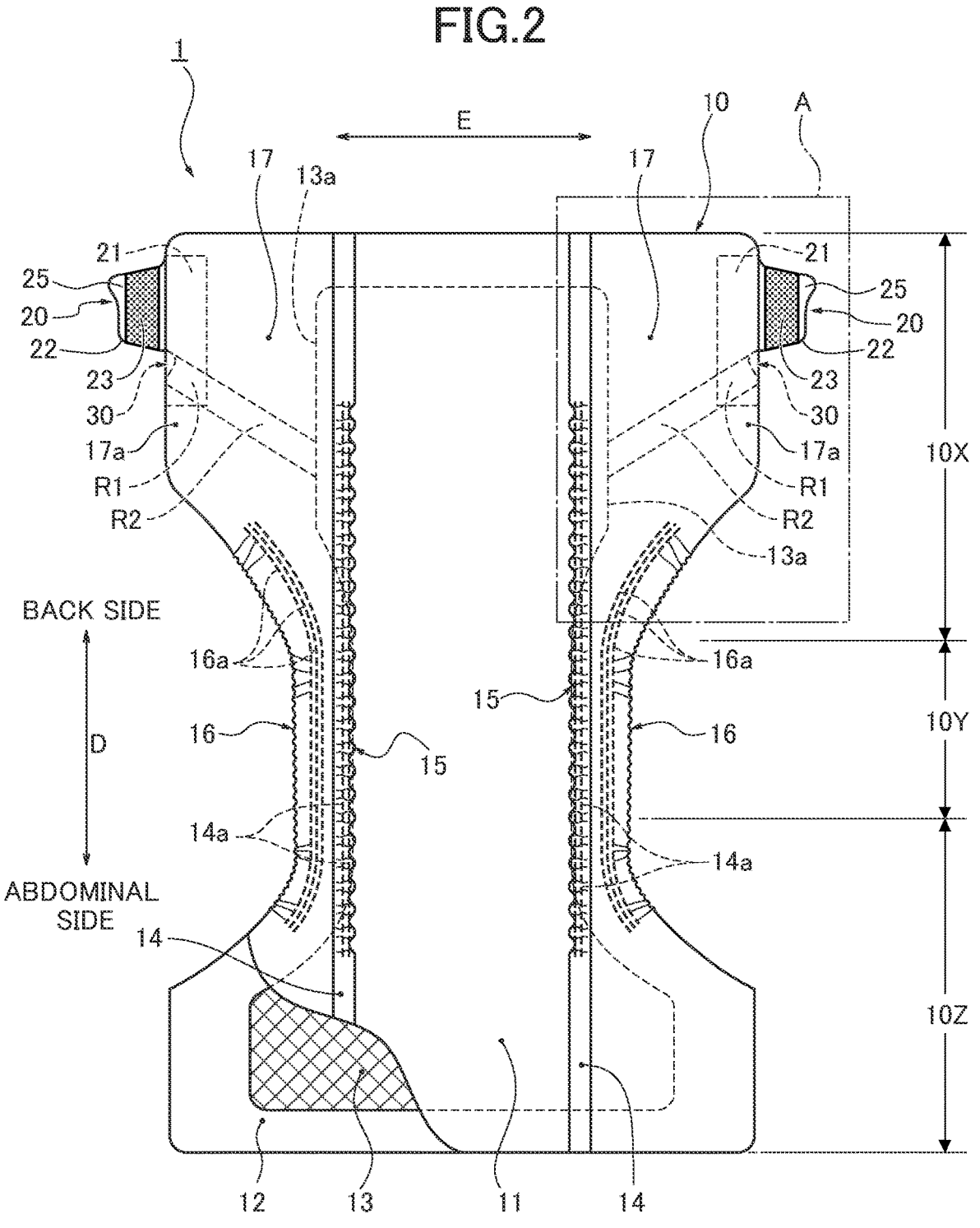
FIG. 2 is a plan view illustrating the disposable diaper in Example 1.

A disposable diaper 1 of Example 1 is a diaper that is attached to a wearer P by a caregiver. As illustrated in FIG. 1, at the time of use of the disposable diaper 1, the wearer P is covered with a diaper body 10 from his or her back through a crotch to his or her abdomen. As illustrated in FIG. 2, the disposable diaper 1 includes the diaper body 10 and fastening tapes 20. The diaper body 10 includes a backside portion 10X, a crotch portion 10Y, and an abdominal side portion 10Z. The fastening tapes 20 are provided in the diaper body 10. The backside portion 10X, the abdominal side portion 10Z, and the crotch portion 10Y between the backside portion 10X and the abdominal side portion 10Z are formed integrally. Note that there are no boundaries or structural differences between the backside portion 10X and the crotch portion 10Y and between the abdominal side portion 10Z and the crotch portion 10Y.

In the disposable diaper 1, a side flap 17 is provided on each side of the backside portion 10X and is attached to the abdominal side portion 10Z via the fastening tape 20. The disposable diaper 1 may be used together with an inner pad set inside the diaper 1.

In the description, a direction that connects the backside portion 10X and the abdominal side portion 10Z is defined as an "extending direction D" while a direction that is orthogonal to the extending direction D is defined as a "width direction E". Furthermore, in the description, the terms "up and down", "left and right", "front and rear", and the like are used with reference to the wearer P. In other words, the extending direction D is a front-rear direction of the diaper body 10. The front side corresponds to an abdominal side of the wearer P, and the rear side corresponds to a back side of the wearer P.

As illustrated in FIG. 2, the diaper body 10 includes a top sheet 11 (a front surface sheet), a back sheet 12 (a back surface sheet), an absorber 13, and a pair of gathered sheets 14.

The top sheet 11 is provided on a body side or inner side of the diaper body 10 to cover a front surface of the absorber 13. The top sheet 11 is liquid permeable, which is a property that allows the liquid to permeate through it. The top sheet 11 is formed of, for example, liquid-permeable non-woven fabric or the like. The top sheet 11 allows body fluid to pass quickly toward the absorber 13.

The back sheet 12 is provided on a cloth side or outer side of the diaper body 10 to cover a back surface of the absorber 13. The back sheet 12 is liquid-impermeable, which is a property that does not allow the liquid to pass through it. The back sheet 12 is formed of, for example, a resin film. The back sheet 12 prevents the body fluid retained by the absorber 13 from passing through it, thereby clothes or the like do not get wet.

The absorber 13 is provided between the top sheet 11 and the back sheet 12 to absorb and retain the liquid (i.e., body fluid) that has passed through the top sheet 11. The absorber 13 is formed with pulp fibers and absorbent polymer particles formed in a sheet and is wrapped by a core wrap sheet (not shown) made of crepe paper, nonwoven fabric, or the like. Note that the absorber 13 is not necessarily wrapped by the core wrap sheet. The absorber 13 has a band shape extending in the extending direction D of the diaper body 10 has a smaller outer shape than those of the top sheet 11 and the back sheet 12. The absorber 13 may be single-layered or multilayered.

The top sheet 11 and the back sheet 12 are layered each other with the absorber 13 provided therebetween, and portions of the sheets 11 and 12 other than regions that overlap the absorber 13 are attached by an adhesive such as a hot melt adhesive, or the like.

For example, water-repellent or liquid-impermeable non-woven fabric may be used for the gathered sheet 14. Each of the gathered sheet 14 has a band shape that extends in the extending direction D. The gathered sheet 14 is provided on each side of the diaper body 10 with the center of the diaper body 10 being located between the pair of the gathered sheets 14 in the width direction E. The first end of the gathered sheet 14 in the width direction E is fixed to the top sheet 11 by an adhesive such as, for example, a hot melt adhesive, welding, or the like. At a second end in the width direction E of the gathered sheet 14, two elongated shaped elastically stretchable members 14a (see FIG. 2) extending in the extending direction D are provided in a predetermined stretched state. For example, thread-shaped or band-shaped synthetic rubber or the like may be used as the elastically stretchable members 14a. The elastically stretchable members 14a extend respectively from the backside portion 10X to the abdominal side portion 10Z. The contraction force of the elastically stretchable members 14a forms gathers at the second end of the gathered sheet 14 in the width direction E to raise or lift the gathered sheet 14 from the top sheet 11. The raised or lifted gathered sheet 14 forms three-dimensional gathers 15. The three-dimensional gathers 15 are deformable to conform to the body of the wearer P, thereby preventing the lateral leakage of the excrement of the wearer P.

Furthermore, the diaper body 10 includes a plurality of elastically stretchable members 16a provided in portions along the groin of the wearer P to extend in the extending direction D in a predetermined stretched state. The elastically stretchable members 16a are elongated shaped, and for example, thread-shaped or band-shaped synthetic rubber or the like may be used for the elastically stretchable members 16a. The contractive force of the elastically stretchable members 16a forms flat gathers 16 in the portions along the groin of the diaper body 10.

The flat gathers 16 extend along the extending direction D of the diaper body 10 with the crotch portion 10Y as a center. As illustrated in FIG. 2, the flat gathers 16 are provided on the outside of the three-dimensional gathers 15 in the width direction E. The flat gathers 16 are deformable to conform to the body of the wearer P. In the diaper body 10, the flat gathers 16 are deformed to improve the fit around the groin of the wearer P.

Moreover, in the diaper body 10, the side flap 17 is formed on each side of the backside portion 10X in the width direction E. Each of the side flaps 17 is formed by the top sheet 11 and the back sheet 12 which extend laterally (outwardly in the width direction E) from a side edge 13a of the absorber 13 in the width direction E. Note that in the side flap 17, the entire surface of the top sheet 11 is bonded to the back sheet 12. In addition, as illustrated in FIG. 2, the side flap 17 on each side of the backside portion 10X is provided with a fastening tape 20.

The fastening tapes 20 may be formed of, for example, non-woven fabric, a plastic film, poly-laminate non-woven fabric having a surface covered with a thin polyethylene film, paper, or a sheet material made of these composite materials. The fastening tapes 20 are used to pull the side flap 17 when a caregiver applies the disposable diaper 1 to the wearer P. A material used for the fastening tapes 20 has a basis weight (or basis weight) higher than those of the top sheet 11, the back sheet 12, or the like to prevent undesirable or unexpected tearing or stretching during use. In addition, each of the fastening tape 20 includes a fixed portion 21 and a single protruding piece 22.

The fixed portion 21 is fixed to a side end 17a of the side flap 17. The entire surface of the fixed portion 21 is fixed to the side flap 17 in this embodiment. However, the fixed portion 21 may be fixed to the side flap 17 in a state where the fixed portion 21 partially protrudes from the side end 17a. The fixed portion 21 is fixed to an outer side (i.e., cloth side) of the side flap 17, that is, to the back sheet 12 in this embodiment. The fixed portion 21 may be fixed to the front and back surfaces of the side flap 17 to sandwich the side flap 17. Alternatively, the fixed portion 21 may be fixed to an inner side (i.e., body side) of the side flap 17, that is to the top sheet 11. The fixed portion 21 is fixed to the side flap 17 by an adhesive such as a hot melt adhesive, or welding. Furthermore, the fixed portion 21 has a rectangular shape in a plan view and extends in the extending direction D of the diaper body 10.

The protruding piece 22 is formed by partially extending an outer edge 21a (see FIG. 3) of the fixed portion 21 outwardly in the width direction E. In other words, the protruding piece 22 extends from the outer edge 21a of the fixed portion 21 to the outside of the diaper body 10 in the width direction E. Note that the "outer edge 21a of the fixed portion 21" is an outer side edge of the fixed portion 21 in the width direction E. In addition, the protruding piece 22 protrudes from the side flap 17 to a side of the diaper body 10, that is, outwardly in the width direction E.

Furthermore, the fixed portion 21 is provided with only one protruding piece 22. The protruding piece 22 has a substantially rectangular shape that is smaller than the fixed portion 21 in a plan view. In addition, the protruding pieces 22 are configured to be grasped or held by a caregiver when the disposable diaper 1 is applied or attached to the wearer P.

Furthermore, an engaging member 23 is provided on an inner surface (i.e., surface on the body side) of the protruding piece 22. The engaging member 23 removably and detachably engages with a target tape 24 provided on the outer side (i.e., cloth side) of the abdominal side portion 10Z of the diaper body 10.

As the engaging member 23, a hook member of a hook and loop fastener or an adhesive tape is used. Any material, shape, or the like of the engaging member 23 may be used as long as the engaging member 23 can repeatedly engage with and disengage from the target tape 24. For example, in a case where the engaging member 23 is the hook member of the hook and loop fastener, a sheet having, on its surface, a large number of loop threads that tangle or interlock with the hook member can be used as the target tape 24. In a case where the engaging member 23 is the adhesive tape, the target tape 24 may be, for example, a smooth and/or flat sheet applied with a peeling process on its surface. Moreover, in a case where the engaging member 23 consists of the hook member, and the outer side (i.e., cloth side) surface of the back sheet 12 is made of non-woven fabric, the target tape 24 may be omitted. In this case, the engaging member 23 is entangled with the fibers of the back sheet 12 to be fastened.

In addition, in the disposable diaper 1 of Example 1, a cutout or notch 30 is formed in the fixed portion 21 of the fastening tape 20. Furthermore, a mark 25 is formed in the protruding piece 22 of the fastening tape 20.

The mark 25 indicates a position of the protruding piece 22 to be grasped or held by a caregiver when the disposable diaper 1 is applied to the wearer. The mark 25 is formed at an outer side edge 22a of the protruding piece 22 in the width direction E. The mark 25 in Example 1 is formed by outwardly protruding an upper portion of the outer side edge 22a of the protruding piece 22 (i.e., a corner portion on an upper side of the protruding piece 22) in a semicircular shape in the width direction E.

Note that the engaging member 23 is provided in an intermediate portion of the protruding piece 22 in the width direction E, which is a position that does not interfere with the mark 25. Therefore, the mark 25 does not engage with the target tape 24, and accordingly, it is easily pinched or held to disengage the fastening tape 20. Therefore, the mark 25 does not engage with the target tape 24 to be easily pinched or held to release the fastening tape 20.

Figure 4:
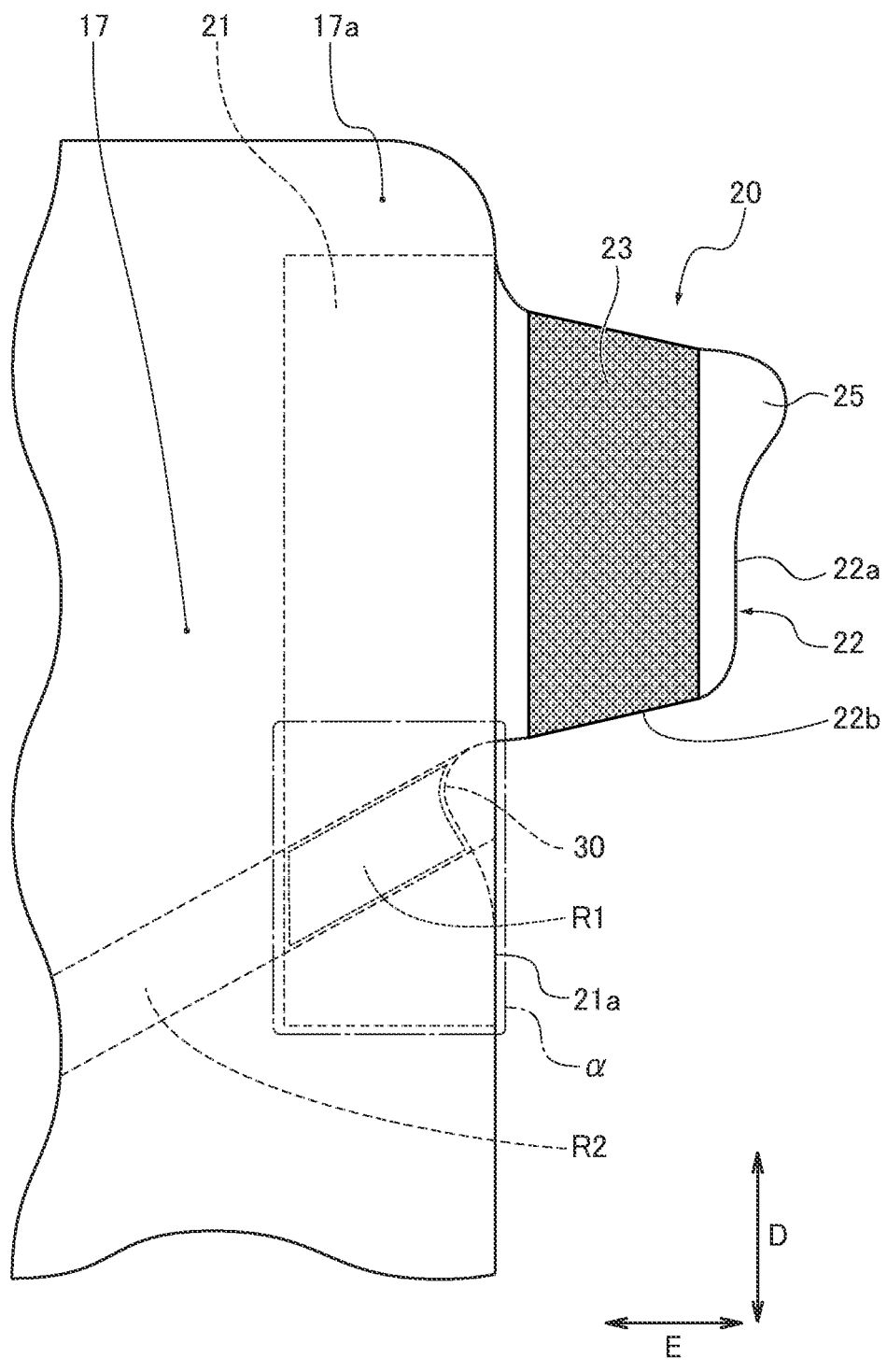
FIG. 4 is an enlarged view of a portion B in FIG. 3.

Each of the notch 30 is provided at the outer edge 21a of the fixed portion 21 in the width direction E and is recessed inwardly from the outer edge 21a in the width direction E. In other words, the notch 30 is formed by partially cutting out the outer edge 21a of the fixed portion 21 inwardly in an arc shape in the width direction E. The notch 30 is formed in a lower region a (i.e., the region enclosed by a dashed-and-dotted line in FIG. 4) of the fixed portion 21. In this embodiment, the notch 30 is formed in a position that is continuous from a lower end 22b of the protruding piece 22. In other words, the protruding piece 22 and the notch 30 are formed in an integrally continuous curved shape in a plan view. The term "lower region a" corresponds to a region lower than the position of the fixed portion 21 from which the protruding piece 22 protrudes, that is, a region lower than the lower end 22b of the protruding piece 22 (i.e., the region on a side of the crotch portion 10Y and a leg side of the wearer P).

In addition, each of the marks 25 is formed in an upper corner of the protruding piece 22. The mark 25 and the notch 30 face each other across the protruding piece 22 since the notch 30 is formed at the outer edge 21a of the fixed portion 21 in the width direction E continuously from the lower end 22b of the protruding piece 22. In other words, a position where the mark 25 is formed and a position where the notch 30 is formed are approximately arranged on the same diagonal line of the protruding piece 22.

Figure 3:
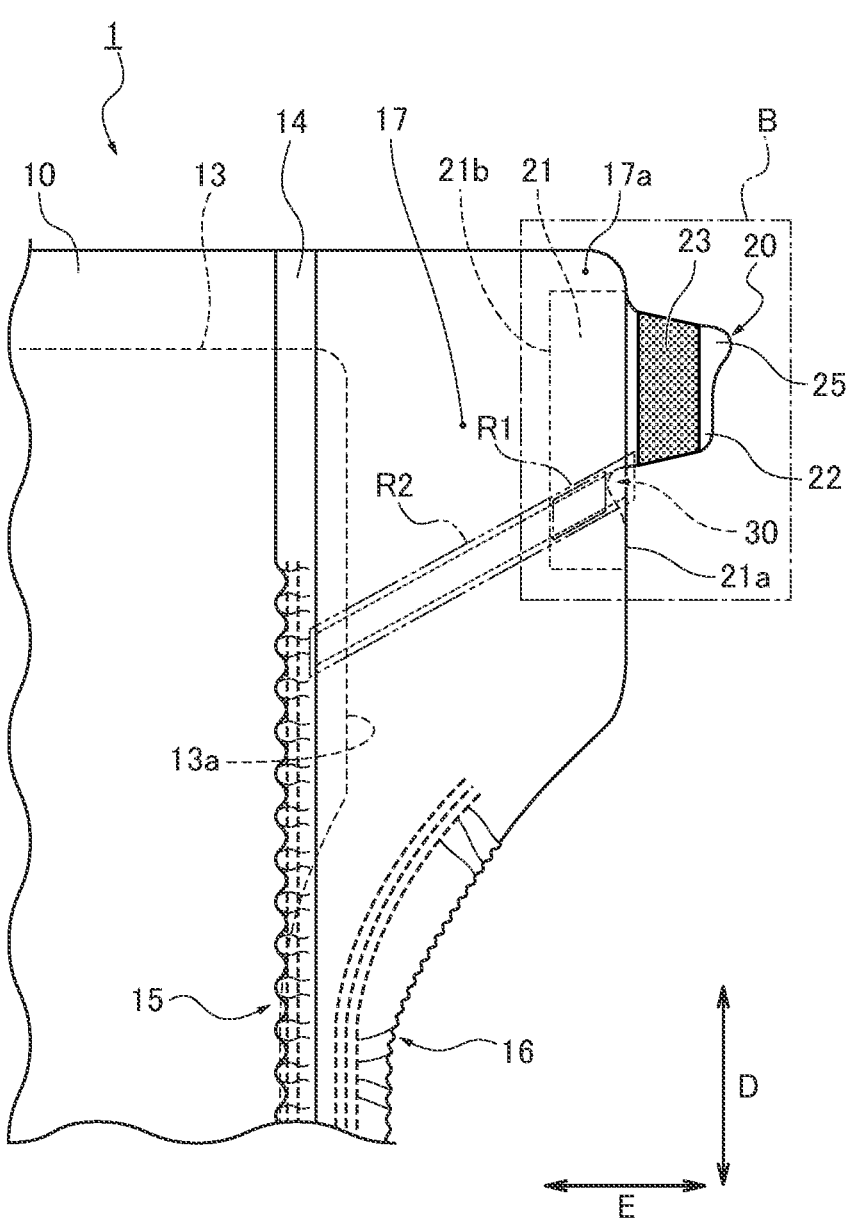
FIG. 3 is an enlarged view of a portion A in FIG. 2.

Moreover, in the disposable diaper 1 of Example 1, each of the fixed portions 21 includes a non-fixed region R1 (a region enclosed by a broken line in FIG. 4), and each of the side flaps 17 includes a non-adhesion region R2 (a region enclosed by a dashed-and-double-dotted line in FIG. 3).

The non-fixed region R1 is a region that is not fixed to the side flap 17 in the fixed portion 21. The non-fixed region R1 extends from the notch 30 to an inner edge 21b of the fixed portion 21 in the width direction E and extends obliquely downward through the lower region a. Note that the extending direction of the non-fixed region R1 is not limited to the direction illustrated in FIG. 3, and may be set in any direction as long as the extending direction passes through the lower region a of the fixed portion 21.

The non-adhesion region R2 is a region where the top sheet 11 and the back sheet 12 are not bonded to each other in the side flap 17 that is formed by layering the top sheet 11 and the back sheet 12 together. The non-adhesion region R2 extends from a position overlapping the notch 30 to a position where the gathered sheet 14 is provided and extends in the same direction as the non-fixed region R1 (i.e., obliquely downward direction through the lower region a). Therefore, the non-fixed region R1 and the non-adhesion region R2 overlap each other.

Note that the non-adhesion region R2 may extend in a direction different from the extending direction of the non-fixed region R1. The extending direction of the non-adhesion region R2 is not limited to the direction illustrated in FIG. 3 and may be set in any direction as long as the direction passes through the lower region a of the fixed portion 21. Moreover, the non-adhesion region R2 may extend from the side end 17a of the side flap 17 to an intermediate position (i.e., a position before the gathered sheet 14) of the side flap 17.

The effects of the disposable diaper 1 of Example 1 are described below.

In applying the disposable diaper 1 of Example 1 to the wearer P, a caregiver first unfolds the diaper body 10 of the disposable diaper 1, and places the diaper body 10 over the body of the wearer P who is in a supine position state. At this time, the caregiver places the backside portion 10X of the diaper body 10 against the back of the wearer P. Next, the caregiver covers the abdomen of the wearer P with the abdominal side portion 10Z of the diaper body 10. Subsequently, the caregiver holds the protruding pieces 22 and pulls the side flaps 17 via the fastening tapes 20 to fit the backside portion 10X to the body of the wearer P. Then, the caregiver fastens the engaging members 23 in the protruding pieces 22 onto the target tape 24 while pulling the side flaps 17. As a result, the side flaps 17 are bound together with the abdominal side portion 10Z, and the disposable diaper 1 is worn by the wearer P.

Figure 5:
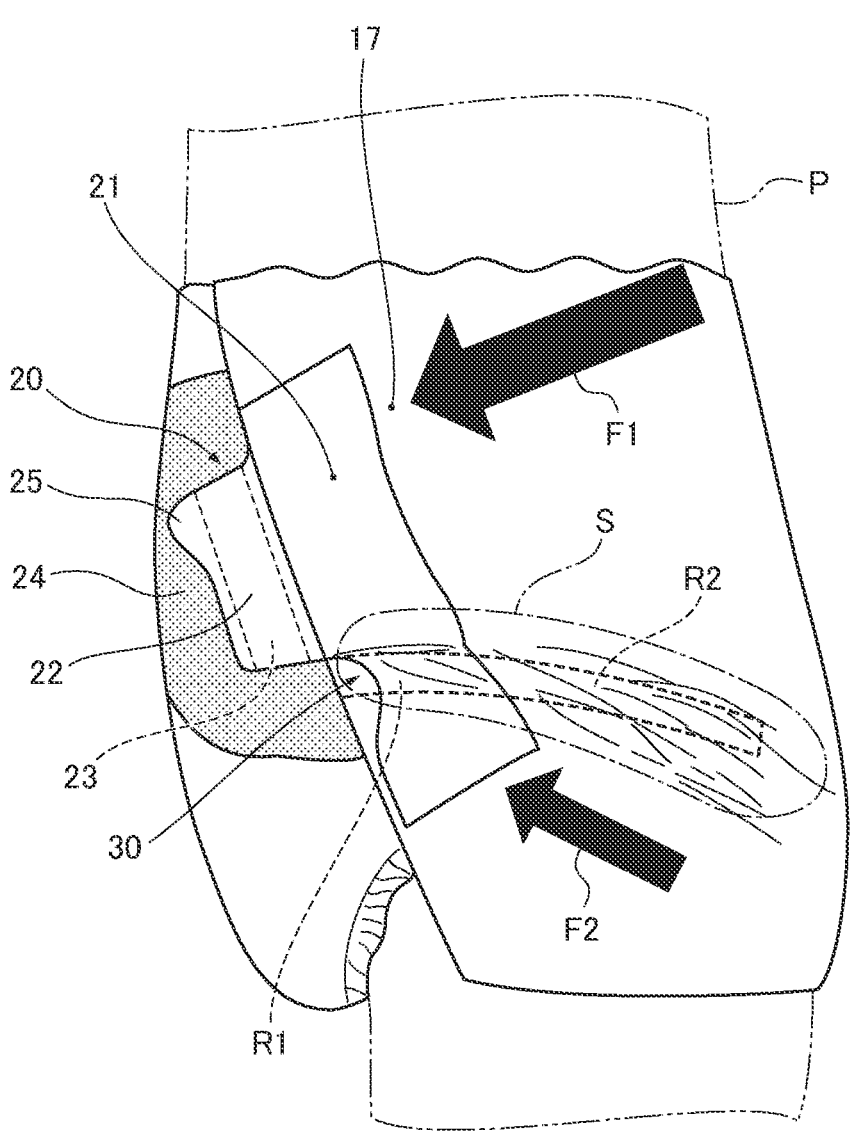
FIG. 5 is an explanatory diagram illustrating wrinkles generated by the use of the disposable diaper in Example 1.

Here, each of the fastening tapes 20 of the disposable diaper 1 of Example 1 is provided with the notch 30 formed in the lower region a of the fixed portion 21 that is located on the side closer to the leg of the wearer P than the protruding piece 22. Therefore, the fastening tape 20 does not overlap a portion of the side end 17a of the side flap 17 where the notch 30 overlaps. In other words, the lower region a of the fixed portion 21 has a portion with decreased rigidity. Therefore, when each of the side flaps 17 is pulled, the lower side portion (i.e., leg side of the wearer P) of the protruding piece 22 where the notch 30 overlaps is appropriately deformed. As a result, at the time of using the disposable diaper 1, as illustrated in FIG. 5, a portion of the side flap 17 that overlaps the notch 30 is bent to generate folds or wrinkles S around the notch 30. In addition, the lower portion of the side flap 17 is prevented from being loosening or floating to thereby fit the body of the wearer P, and accordingly, the fit of the diaper body 10 around the legs can be improved.

Furthermore, in the disposable diaper 1 of Example 1, the marks 25 are formed on the outer side edges 22a of each of the protruding pieces 22 in the width direction E. Therefore, in the disposable diaper 1, the caregiver can hold the protruding pieces 22 at the positions where the marks 25 are formed. In this embodiment, the caregiver can hold the upper portions of the outer side edges 22a of the protruding pieces 22 (i.e., upper corner portions of the protruding pieces 22). Furthermore, the caregiver can easily pull the side flaps 17 obliquely downward in the width direction E by holding the positions where the marks 25 are provided and pulling the fastening tapes 20. In other words, in the disposable diaper 1, the marks 25 formed on the outer side edges 22a of the protruding pieces 22 in the width direction E guide the caregiver to pull the side flaps 17 obliquely downward below the width direction E, thereby improving the fit of the diaper body 10 around the waist.

On the other hand, in the disposable diaper 1 of Example 1, the notches 30 in the fixed portions 21 are provided to face the marks 25 across the protruding pieces 22, respectively. Therefore, when each of the side flaps 17 is pulled obliquely downward and a first force F1 directed obliquely downward acts on the upper portion of the side flap 17, a second force F2 in an obliquely upward direction toward the notch 30 acts on the lower portion of the side flap 17. In other words, the force (second force F2) that pulls the lower side (leg side) of the fastening tape 20 upward is applied to the side flap 17.

Therefore, the wrinkles S around each of the notches 30 extend obliquely downward from the notch 30. The wrinkles S that extend obliquely downward from each of the notches 30 are generated in each of the side flaps 17. This prevents the lower portions of the side flaps 17 from loosening or floating, and accordingly, the fit of the diaper body 10 around the legs can be improved.

Furthermore, in the disposable diaper 1 of Example 1, the fixed portion 21 of the fastening tape 20 includes the non-fixed region R1 that is not fixed to the side flap 17. In the non-fixed region R1, the fixed portion 21 is separated from the side flap 17, and in the side flap 17, the rigidity in the non-fixed region R1 is lower than that in a portion that is fixed to the fixed portion 21. Therefore, the side flap 17 can be easily deformed in the non-fixed region R1.

In addition, the non-fixed region R1 extends obliquely downward from the notch 30 through the lower region a of the fixed portion 21, and therefore, the first force F1 and the second force F2 that act on the side flap 17 can be focused on the notch 30. As a result, the wrinkles S extending in the obliquely upward direction toward the notch 30 can be easily generated in the lower portion of the side flap 17, thereby improving the fit of the diaper body 10 around the legs.

Moreover, in the disposable diaper 1 of Example 1, each of the side flaps 17 is formed by laminating the top sheet 11 and the back sheet 12, wherein the top sheet 11 is bonded to the back sheet 12. In addition, each of the side flaps 17 includes the non-adhesion region R2 where the top sheet 11 is not bonded to the back sheet 12.

In the non-adhesion region R2, the top sheet 11 is separated from the back sheet 12, and in the side flap 17, the rigidity in the non-adhesion region R2 is lower than that in the portion where the top sheet 11 is bonded to the back sheet 12. Therefore, the side flap 17 can be easily deformed in the non-adhesion region R2. Furthermore, the non-adhesion region R2 extends obliquely downward from the position where the notch 30 overlaps through the lower region a of the fixed portion 21. Therefore, the wrinkles S generated in the side flap 17 to extend in the obliquely upward direction toward the notch 30 can be expanded or developed toward the center in the width direction E of the backside portion 10X. As a result, the fit of the diaper body 10 around the legs can be further improved.

Example 2

Figure 6:
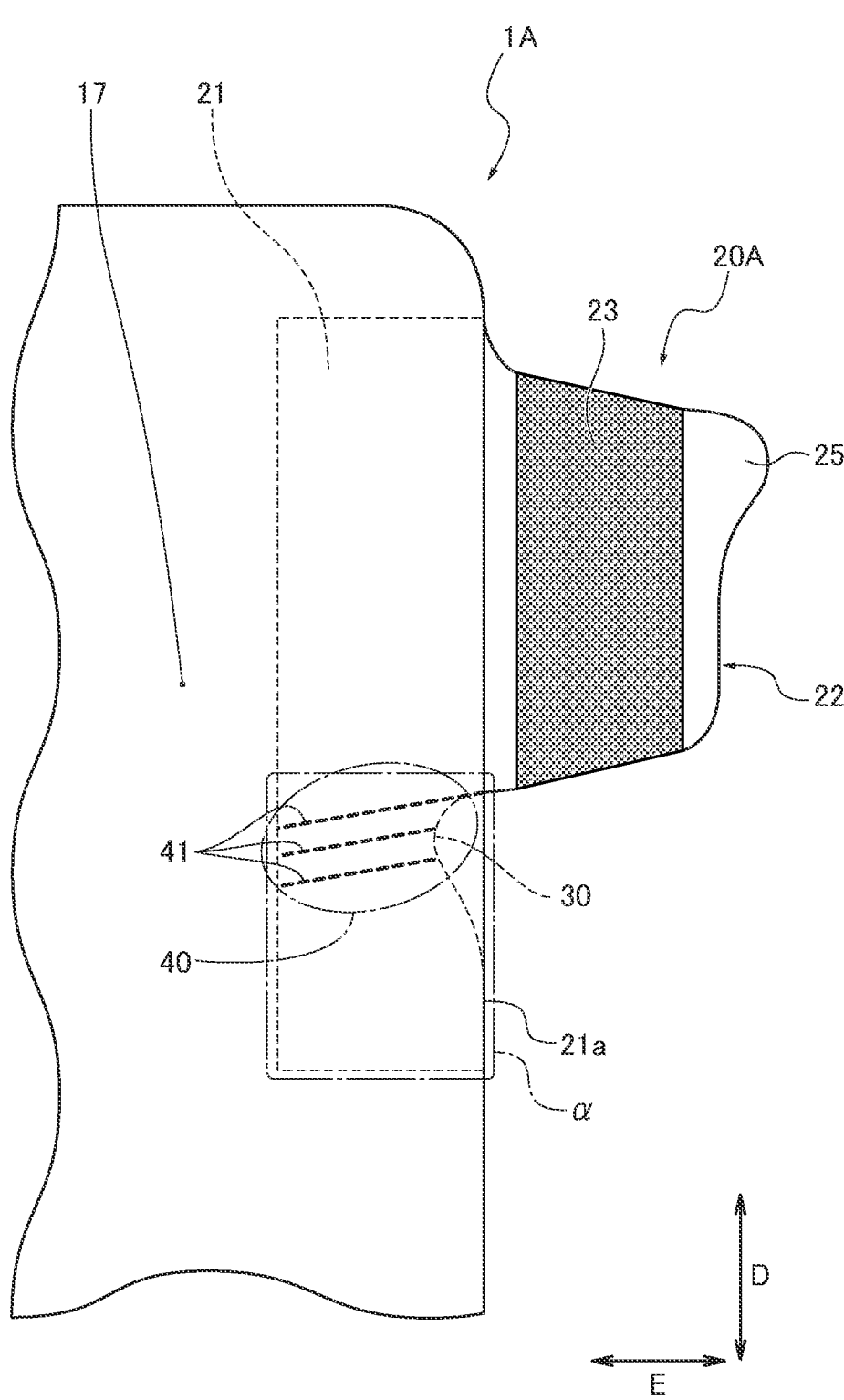
FIG. 6 is an enlarged view illustrating a principal portion of the disposable diaper in Example 2.

In a disposable diaper 1A of Example 2, as illustrated in FIG. 6, the notch 30 is formed in a fixed portion 21 of a fastening tape 20A, and a fragile structure 40 is formed at the periphery of the notch 30 to suppress the rigidity of the fastening tape 20A. Note that the configuration of the disposable diaper 1A of Example 2 other than the fastening tape 20A is similar to that of the disposable diaper 1 of Example 1. Therefore, a detailed description of such a configuration is omitted.

In the disposable diaper 1A of Example 2, the fragile structure 40 in the fastening tape 20A consists of a plurality of perforations 41 (three perforations in this embodiment) formed in the fixed portion 21. Each of the perforations 41 includes cut portions that penetrate the fixed portion 21 and uncut portions that do not penetrate the fixed portion 21 which are alternately arranged in a predetermined direction passing through the lower region a of the fixed portion 21. Furthermore, the plurality of perforations 41 constituting the fragile structure 40 are aligned in the extending direction D at predetermined intervals.

The fixed portion 21 of the fastening tape 20A includes the fragile structure 40 consisting of the plurality of perforations 41, and accordingly, the rigidity in the portion where the fragile structure 40 is formed is reduced compared to that in a portion where the fragile structure 40 is not formed. In other words, in the fixed portion 21 of the fastening tape 20A, the rigidity is suppressed at the periphery of the notch 30.

The effects of the disposable diaper 1A of Example 2 are described below.

In the disposable diaper 1A of Example 2, when the caregiver pulls the side flaps 17 obliquely downward, the first force F1 directed obliquely downward acts on the upper portions of the side flaps 17. Furthermore, the second force F2 in the obliquely upward direction toward the notch 30 acts on the lower portions of the side flaps 17. In addition, the notches 30 are formed in the fixed portions 21 of the fastening tapes 20, and therefore, the folds or wrinkles S extending obliquely downward from the notches 30 are generated in the side flaps 17. As a result, the disposable diaper 1A of Example 2 can suppress any loosening or floating in the lower portions of the side flaps 17, thereby improving the fit of the diaper body 10 around the legs.

Furthermore, in the disposable diaper 1A of Example 2, the fragile structure 40 is formed at the periphery of the notch 30 formed in the fixed portion 21. The fragile structure 40 suppresses the rigidity of the fixed portion 21. Therefore, in the fixed portion 21, the portion where the fragile structure 40 is formed can be deformed more easily than the portion where the fragile structure 40 is not formed. Therefore, when the side flap 17 is pulled, and the wrinkles S are generated in the side flap 17 with the notch 30 as the center, the portion in the fixed portion 21 where the fragile structure 40 is formed, that is, the lower region a of the fixed portion 21, can be easily deformed. As a result, the periphery of the notch 30 is deformed to conform to the body of the wearer P, thereby improving the wearing comfort of the diaper body 10.

Note that the fragile structure 40 formed in the fixed portion 21 to suppress the rigidity at the periphery of the notch 30 is not limited to the one having the plurality of perforations 41. The fragile structure 40 may have a configuration that suppresses the rigidity of the fixed portion 21 at the periphery of the notch 30. For example, as in a first variation illustrated in FIG. 7, a fragile structure 40A may be configured by not providing the fixed portion 21 in a portion below a straight line L that connects a position where the notch 30 is formed to a position where the mark 25 is formed (i.e., a portion closer to the side of the crotch portion 10Y and the leg side of the wearer P).

Figure 7:
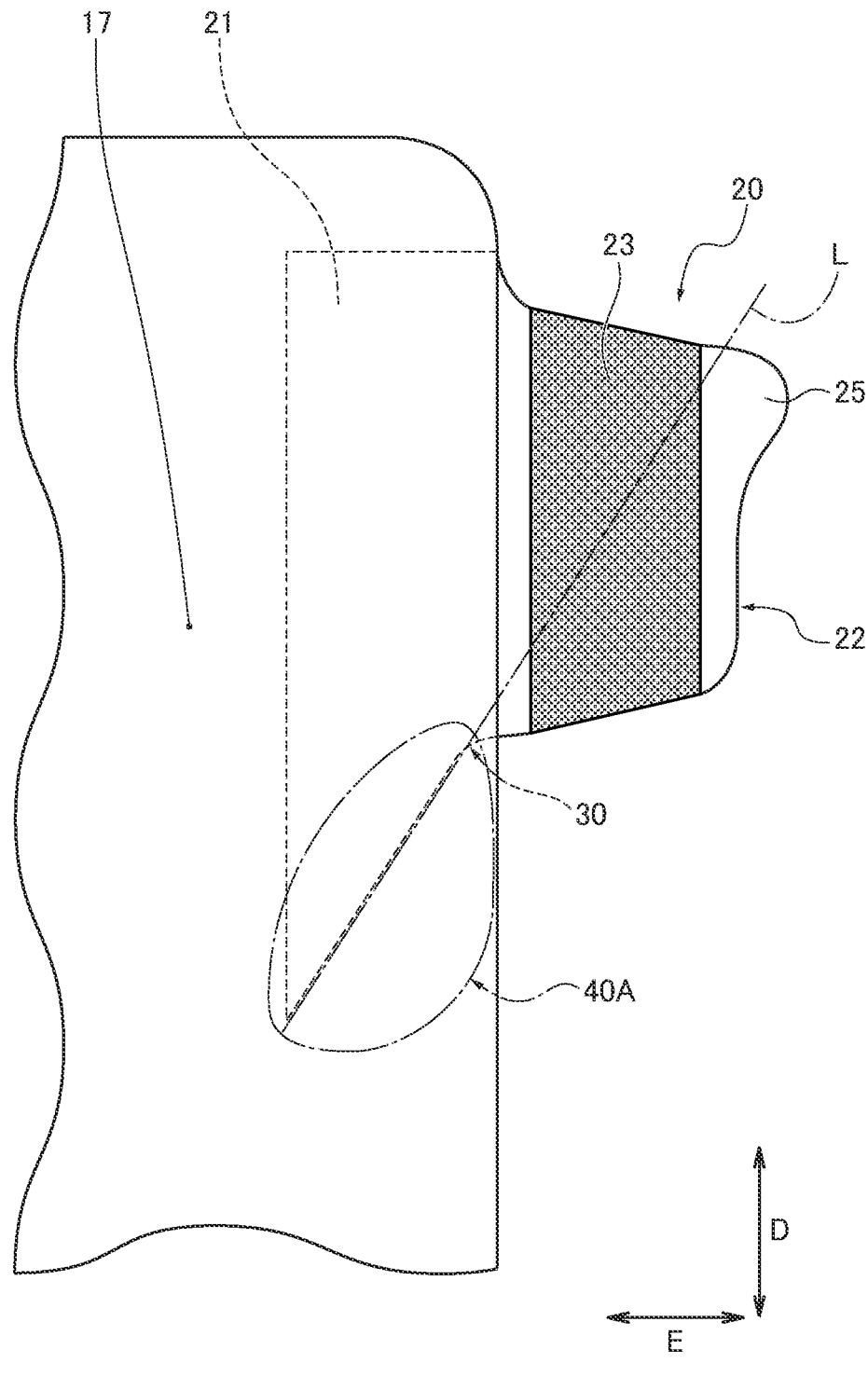
FIG. 7 is an enlarged view of a principal portion illustrating a variation of the disposable diaper in Example 2.

Each of the fixed portion 21 includes the fragile structure 40A of the first variation illustrated in FIG. 7, and therefore, the area of the fixed portion 21 can be smaller than that in a case where the fragile structure 40 consists of, for example, the perforations 41. Therefore, the area of the side flap 17 where the rigidity is increased by the fixed portion 21 can be made small so that the side flap 17 can be easily deformed. Thus, the periphery of the notch 30 is deformed to conform to the body of the wearer P, thereby improving the wearing comfort of the diaper body 10.

The disposable diaper of the present disclosure has been described above in accordance with Examples 1 and 2. However, the specific configuration of the disposable diaper is not limited to these examples, and design changes, combinations of respective examples, additions, or the like are acceptable without departing from the scope of the invention according to each claim.

Figure 8:
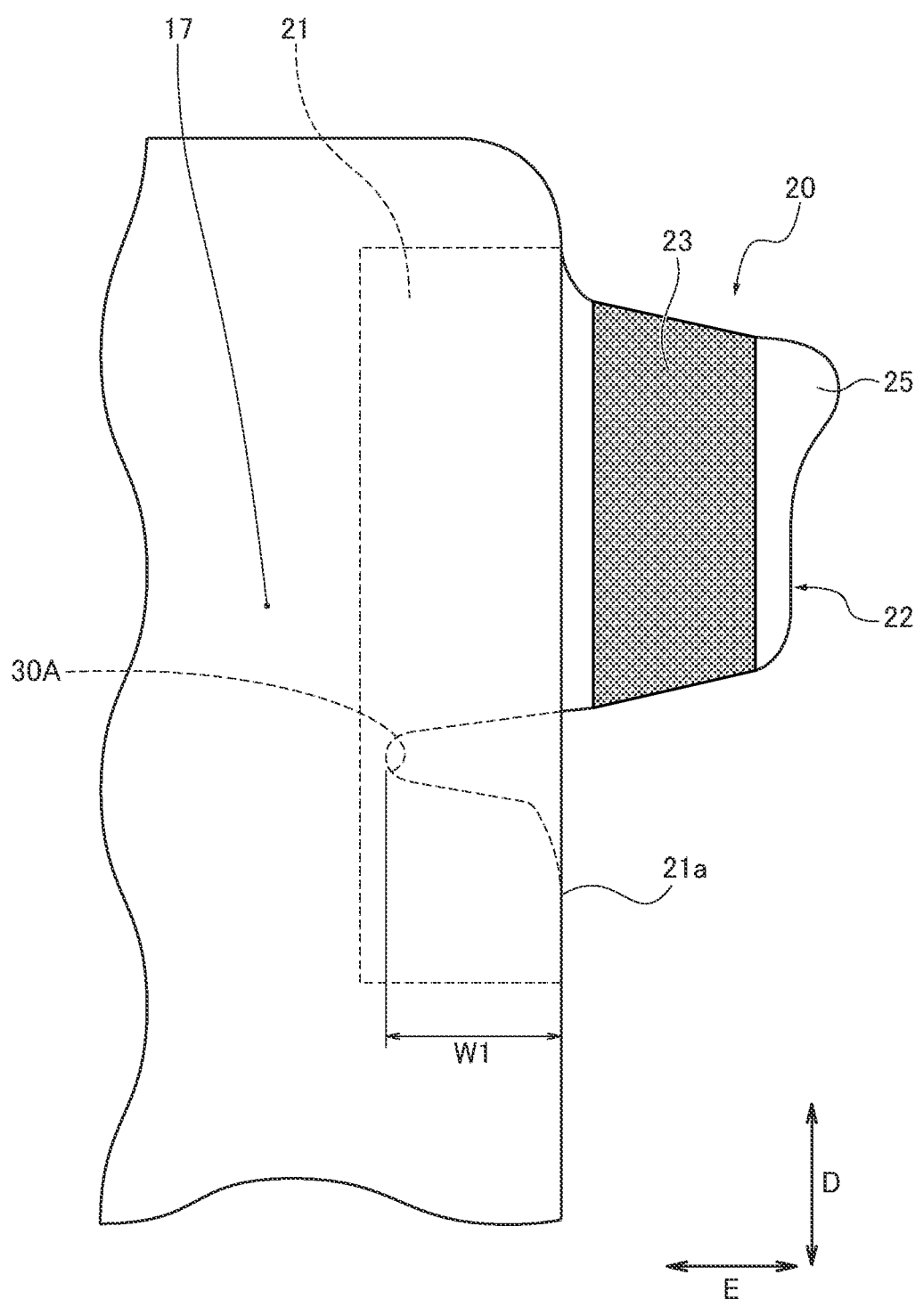
FIG. 8 is an enlarged view of a principal portion illustrating a first variation of a disposable diaper.

For example, as in the first variation as illustrated in FIG. 8, a notch 30A may be provided to have a length W1 extending inwardly from an outer edge 21a of the fixed portion 21 in the width direction E wherein the length W1 is longer than the length of the notch 30 in Example 1. In this case, the area of the fixed portion 21 of the fastening tape 20 can be smaller than that of the fixed portion 21 in Example 1 where the notch 30 is formed. This reduces an area of the side flap 17 with the rigidity increased by the fixed portion 21 similar to the case where the fragile structure 40A that suppresses the rigidity at the periphery of the notch 30 is provided in the first variation. Therefore, the side flap 17 can be easily deformed, and the periphery of the notch 30A can be deformed to conform to the body of the wearer P, thereby improving the wearing comfort of the diaper body 10.

Furthermore, in the disposable diaper 1 of Example 1, the mark 25 provided in the protruding piece 22 is formed by protruding the outer side edge 22a of the protruding piece 22 outward in the width direction E. However, the mark 25 may be formed to guide a caregiver to hold a position where the mark 25 is formed. Therefore, the mark 25 may be formed, for example, by coloring an upper portion of the outer side edge 22a of the protruding piece 22.

Furthermore, the position where each of the marks 25 is formed is not limited to the upper portion of the outer side edge 22a of the protruding piece 22 (i.e., the upper corner portion of the protruding piece 22). Each of the marks 25 may be formed in any position as long as the position is desirable for a caregiver to grasp or hold.

Moreover, in the disposable diaper 1 of Example 1, each of the side flaps 17 is formed by laminating the top sheet 11 and the back sheet 12, wherein the top sheet 11 is the front surface sheet and the back sheet 12 is the back surface sheet. However, the configuration of the side flap 17 is not limited to the above. For example, the front surface sheet may consist of the top sheet 11 and the gathered sheet 14 disposed on both sides of the top sheet 11, while the side flap 17 may be formed by laminating the gathered sheet 14 and the back sheet 12.

The invention claimed is:

1. A disposable diaper comprising:
  a diaper body that comprises a front surface sheet, a back surface sheet, and an absorber disposed between the front surface sheet and the back surface sheet, the diaper body extending from a backside portion of the diaper body to an abdominal side portion of the diaper body;
  a side flap that is provided in each of side portions of the backside portion, the side flap extending outward beyond the absorber in a width direction of the diaper body; and
  a fastening tape that is provided in the side flap to be fastened to the abdominal side portion when the diaper body is used;
  wherein the fastening tape comprises:
    a fixed portion that is fixed to the side flap; and
    a protruding piece that extends outward from the fixed portion in the width direction;
  wherein the fixed portion comprises a notch in a lower region of the fixed portion that is closer to a leg side of a wearer than the protruding piece, the notch being recessed from an outer edge in the width direction toward an inner side in the width direction,
  wherein the fixed portion comprises a non-fixed region that is not fixed to the side flap, and
  wherein the non-fixed region extends from the notch in a direction passing through the lower region of the fixed portion.

2. A disposable diaper comprising:
  a diaper body that comprises a front surface sheet, a back surface sheet, and an absorber disposed between the front surface sheet and the back surface sheet, the diaper body extending from a backside portion of the diaper body to an abdominal side portion of the diaper body;
  a side flap that is provided in each of side portions of the backside portion, the side flap extending outward beyond the absorber in a width direction of the diaper body; and
  a fastening tape that is provided in the side flap to be fastened to the abdominal side portion when the diaper body is used;
  wherein the fastening tape comprises:
    a fixed portion that is fixed to the side flap; and
    a protruding piece that extends outward from the fixed portion in the width direction;
  wherein the fixed portion comprises a notch in a lower region of the fixed portion that is closer to a leg side of a wearer than the protruding piece, the notch being recessed from an outer edge in the width direction toward an inner side in the width direction;
  wherein the side flap is formed by laminating the front surface sheet and the back surface sheet, and comprises a non-adhesion region where the front surface sheet is not bonded to the back surface sheet, and wherein the non-adhesion region extends from a position where the notch overlaps in a direction passing through the lower region of the fixed portion.

3. A disposable diaper comprising:

a diaper body that comprises a front surface sheet, a back surface sheet, and an absorber disposed between the front surface sheet and the back surface sheet, the diaper body extending from a backside portion of the diaper body to an abdominal side portion of the diaper body;

a side flap that is provided in each of side portions of the backside portion, the side flap extending outward beyond the absorber in a width direction of the diaper body; and a fastening tape that is provided in the side flap to be fastened to the abdominal side portion when the diaper body is used;

wherein the fastening tape comprises:

a fixed portion that is fixed to the side flap; and a protruding piece that extends outward from the fixed portion in the width direction;

wherein the fixed portion comprises a notch in a lower region of the fixed portion that is closer to a leg side of a wearer than the protruding piece, the notch being recessed from an outer edge in the width direction toward an inner side in the width direction; and wherein the fixed portion comprises a fragile structure at a periphery of the notch, the fragile structure suppressing rigidity of the fastening tape.

* * * * *